(12) United States Patent
Bachellier

(10) Patent No.: US 9,682,348 B2
(45) Date of Patent: Jun. 20, 2017

(54) IMPELLER APPARATUS AND DISPERSION METHOD

(71) Applicant: Enevor Inc., Albuquerque, NM (US)

(72) Inventor: Carl Roy Bachellier, Dundas (CA)

(73) Assignee: Enevor Inc., Albuquerque, NM (US)

( * ) Notice: Subject to any disclaimer, the term of this patent is extended or adjusted under 35 U.S.C. 154(b) by 322 days.

(21) Appl. No.: 14/298,737

(22) Filed: Jun. 6, 2014

(65) Prior Publication Data

US 2014/0349379 A1    Nov. 27, 2014

Related U.S. Application Data

(63) Continuation-in-part of application No. PCT/CA2012/050873, filed on Dec. 5, 2012.
(Continued)

(51) Int. Cl.
*B01F 3/04* (2006.01)
*B01F 7/22* (2006.01)
(Continued)

(52) U.S. Cl.
CPC ...... *B01F 3/04539* (2013.01); *B01F 3/04439* (2013.01); *B01F 3/04531* (2013.01);
(Continued)

(58) Field of Classification Search
CPC .............. B01F 3/04439; B01F 3/04531; B01F 3/04539; B01F 7/0015; B01F 7/00291;
(Continued)

(56) References Cited

U.S. PATENT DOCUMENTS 344,534 A * 6/1886 Madsen .............. B01F 3/04531
261/87
665,580 A * 1/1901 Price ................... B01F 5/0684
261/87
(Continued)

FOREIGN PATENT DOCUMENTS

CA      1259068 A1    9/1989
CN      202506329     10/2012
(Continued)

OTHER PUBLICATIONS

Jones, et al., "Pumping Station Design: Revised 3rd Edition", Elsevier, Inc., 2008, 11.39.

*Primary Examiner* — Charles Bushey
*Assistant Examiner* — Scott Bushey
(74) *Attorney, Agent, or Firm* — Philip D. Askenazy; Deborah A. Peacock; Peacock Myers, P.C.

(57) ABSTRACT

A method and apparatus for dispersing and entraining and controlling the residence time, absorption and release of gas bubbles or particles in a fluid without losing gas utilization efficiency from escaping surface gas events. A mechanical, rotating plurality of hollowed blades that induce both an axial and radial controlled circulatory flow and provide a means of gas introduction into the discharge flow that has a conical helical, axial and radial outward flow from the axis of rotation and allows entrained gas bubbles to be trapped as particles and recirculated by means of a circulatory flow back into the intake vortex of said mechanical, rotating plurality of blades. The flow is characterized by a forced intake vortex caused by a low pressure zone with a radial component, and subsequent axial component drawing fluid in a circular fashion toward the eye of the rotating device and impelling fluid.

6 Claims, 6 Drawing Sheets

Related U.S. Application Data

(60) Provisional application No. 61/567,151, filed on Dec. 6, 2011.

(51) Int. Cl.

| | | |
|---|---|---|
| *B01F 7/00* | (2006.01) | |
| *C02F 1/72* | (2006.01) | |
| *C02F 1/78* | (2006.01) | |
| *C10G 33/06* | (2006.01) | |
| *C12N 1/12* | (2006.01) | |

(52) U.S. Cl.
CPC ............ *B01F 7/003* (2013.01); *B01F 7/0015* (2013.01); *B01F 7/00291* (2013.01); *B01F 7/00341* (2013.01); *B01F 7/22* (2013.01); *C02F 1/727* (2013.01); *C02F 1/78* (2013.01); *C10G 33/06* (2013.01); *C12N 1/12* (2013.01); *B01F 2003/04546* (2013.01); *B01F 2215/0052* (2013.01); *C02F 2305/023* (2013.01)

(58) Field of Classification Search
CPC ........ B01F 7/003; B01F 7/00341; B01F 7/22; B01F 2003/04546; B01F 2215/0052; C02F 1/727; C02F 1/78; C02F 2305/023; C10G 33/06; C12N 1/12
USPC ................................ 261/87, 91, 93
See application file for complete search history.

(56) References Cited

U.S. PATENT DOCUMENTS

| | | | | |
|---|---|---|---|---|
| 2,008,106 | A * | 7/1935 | Lawrence | A47J 43/044 366/197 |
| 3,442,220 | A | 5/1969 | Mottram | |
| 3,512,762 | A * | 5/1970 | Umbricht | B01F 3/04539 209/169 |
| 3,975,469 | A * | 8/1976 | Fuchs | B01F 3/04539 261/87 |
| 4,200,597 | A * | 4/1980 | Baum | A01C 3/026 210/219 |
| 4,231,974 | A * | 11/1980 | Engelbrecht | B01F 3/04539 209/170 |
| 4,371,480 | A * | 2/1983 | Vos | B01F 3/04539 261/87 |
| 4,776,753 | A | 10/1988 | Weinrib | |
| 4,844,843 | A * | 7/1989 | Rajendren | B01F 3/04539 261/30 |
| 5,051,213 | A * | 9/1991 | Weske | B01F 3/04531 261/120 |
| 5,314,310 | A | 5/1994 | Bachellier | |
| 5,358,671 | A * | 10/1994 | Leiponen | B01F 3/04539 261/87 |
| 5,616,083 | A | 4/1997 | Subbaraman et al. | |
| 5,938,332 | A | 8/1999 | Bachellier | |
| 7,191,613 | B2 | 3/2007 | Lee | |
| 7,784,769 | B2 * | 8/2010 | Hoefken | B01F 3/04773 210/150 |
| 8,240,998 | B2 * | 8/2012 | Otto | F03B 17/00 416/183 |
| 8,506,244 | B2 | 8/2013 | McBride et al. | |
| 2003/0147760 | A1 | 8/2003 | Chiang | |
| 2008/0247267 | A1 | 10/2008 | Clawson et al. | |
| 2009/0169374 | A1 | 7/2009 | Ilves | |
| 2012/0061298 | A1 | 3/2012 | Jameson | |
| 2014/0003929 | A1 | 1/2014 | Favre et al. | |
| 2014/0056696 | A1 | 2/2014 | Kawano et al. | |

FOREIGN PATENT DOCUMENTS

| | | |
|---|---|---|
| CN | 204082577 | 1/2015 |
| EP | 1087146 A2 | 3/2001 |
| GB | 436101 | 10/1935 |
| GB | 0811849 | 4/1959 |
| GB | 2136304 A | 9/1984 |
| KR | 1020110064080 | 6/2011 |
| WO | 2007093668 A1 | 8/2007 |
| WO | 2013082717 A1 | 6/2013 |

\* cited by examiner

IMPELLER APPARATUS AND DISPERSION METHOD

CROSS-REFERENCE TO RELATED APPLICATIONS

This application is a continuation-in-part application of PCT International Application No. PCT/CA2012/050873, entitled "Improved Impeller Apparatus and Dispersion Method", filed on Dec. 5, 2012, which application claims priority to and the benefit of the filing of U.S. Provisional Patent Application Ser. No. 61/567,151, entitled "Improved Impeller Apparatus and Dispersion Method", filed on Dec. 6, 2011. The specifications and claims of these applications are incorporated herein by reference.

BACKGROUND OF THE INVENTION

Field of the Invention (Technical Field)

The present invention relates to an improved impeller apparatus and a dispersion method for dispersing or dissolving gases and other materials into a liquid mixture.

Background Discussion

Note that the following discussion refers to a number of publications and references. Discussion of such publications herein is given for more complete background of the scientific principles and is not to be construed as an admission that such publications are prior art for patentability determination purposes.

Impeller devices for mixing gases and other materials into a liquid mixture have a wide variety of applications in industry. One of the significant limitations and technical challenges that remain with current designs is that typically a large and powerful compressor is required in order to inject sufficient gas into a liquid mixture in order to have a desired level of gas dispersion and mixing with the liquid. Also, while many liquid mixtures are insensitive to mixture with gas at high impeller rotational speeds, the useful properties of other liquid mixtures (e.g. containing organic materials or pharmaceuticals) may be destroyed if gas dispersion and mixing is attempted at mixing speeds that are too high.

For example, an algae liquid mixture in an algae reactor for consuming carbon dioxide ($CO_2$) cannot be mixed at high speeds using conventional propeller mixers, as algae is susceptible to shearing forces and could be killed by being shredded by the blades. In addition, algae reactor vessels using $CO_2$ spargers that bubble $CO_2$ from the bottom of the vessels have been limited in size due to the large amount of energy required to inject enough $CO_2$ to feed the algae before the gas bubbles rise and escape at the top of the algae liquid mixture.

SUMMARY OF THE INVENTION (DISCLOSURE OF THE INVENTION)

The present invention is a method of entraining and dispersing a gas into a liquid mixture in a vessel, comprising providing an impeller configured to form in the liquid mixture a low shear vortex at an intake region of the impeller, and a mirrored low shear vortex at a discharge region of the impeller, thereby to form a circulatory flow of the liquid mixture in the vessel introducing a flow of gas into the circulatory flow of the liquid mixture in the vessel, and controlling at least one of the rotational speed of the impeller and the flow of gas into the liquid mixture to determine the length of time that the gas is entrained and dispersed in the liquid mixture. The introduction of the flow of gas is preferably through a hollow drive shaft for the impeller and/or preferably through a hollowing out of and dispersion holes in the blades of the impeller. The gas is optionally a mixture of exhaust gases including carbon dioxide and the liquid mixture is optionally an algae slurry. The gas to be introduced optionally contains oxygen or ozone and the liquid mixture optionally contains chemical toxins to be removed through active oxidation processing. Optionally the liquid mixture is oil industry wastewater and the method recovers hydrocarbons from the liquid mixture.

The present invention is also a method of mixing a two phase liquid into a single phase liquid in a vessel comprising providing an impeller configured to form in the liquid mixture a low shear vortex at an intake region of the impeller, and a mirrored low shear vortex at a discharge region of the impeller, thereby to form a circulatory flow of the liquid mixture in the vessel, and controlling the rotational speed of the impeller in the liquid mixture to determine the speed of the mixing of the liquid mixture; wherein the impeller comprises a separate upper hub assembly comprising a plurality of arms, each arm comprising a curved outer portion to which a blade is attached.

The present invention is also a method of mixing a plurality of liquids in a vessel comprising providing an impeller configured to form in the liquid mixture a low shear vortex at an intake region of the impeller, and a mirrored low shear vortex at a discharge region of the impeller, thereby to form a circulatory flow of the liquid mixture in the vessel; and controlling the rotational speed of the impeller in the liquid mixture to determine the speed of the mixing of the liquid mixture; wherein the impeller comprises a separate upper hub assembly comprising a plurality of arms, each arm comprising a curved outer portion to which a blade is attached.

The present invention is also an impeller apparatus for entraining and dispersing a gas into a liquid mixture or for mixing a two phase liquid mixture like a single phase liquid in a vessel, comprising: a plurality of blades circumferentially mounted around an upper hub assembly, the blades having a forward intake end and a rearward discharge end and being tapered such that the forward intake end is enlarged relative to the rearward discharge end, the upper hub assembly shaped with a profile configured to minimize disturbance between an intake flow to the blades and an impeller discharge flow, whereby in use the impeller forms in the liquid mixture a low shear vortex at an intake region of the impeller, and a mirrored low shear vortex at a discharge region of the impeller, thereby to form a circulatory flow of the liquid mixture in the vessel. The gas to be entrained and dispersed in the liquid mixture is preferably introduced through a hollow drive shaft of the impeller. The gas to be entrained and dispersed in the liquid mixture is preferably introduced through hollowed-out blades with a plurality of suitably-sized holes located near the rearward discharge edge of the blades.

The present invention is also an impeller apparatus comprising a plurality of blades circumferentially mounted in a conical fashion at their proximal ends to arms of separate upper hub assembly connected to a drive unit, the blades' distal ends being flared out to circumscribe a diameter larger than the upper hub assembly, the blades having a forward intake end directed to the centre of the apparatus and a rearward discharge end and being tapered such that the forward intake end is enlarged relative to the rearward discharge end, whereby in use the impeller forms in the liquid mixture a low shear intake vortex at the centre of the impeller, and a mirrored low shear vortex at a discharge region of the impeller, thereby to form a circulatory flow of the liquid mixture in the vessel. The drive unit preferably comprises a motor and is connected to the impeller via a shaft. The shaft is preferably hollow with outlets placed at the shaft's connection with the impeller to allow the introduction of gas. The blades preferably are hollow with outlets placed along the edges of the blades to allow the introduction of gas. The outlets are optionally placed along the forward edges of the blades or along the rearward edges of the blades.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate embodiments of the present invention and, together with the description, serve to explain the principles of the invention. The drawings are only for the purpose of illustrating certain embodiments of the invention and are not to be construed as limiting the invention. In the drawings.

DETAILED DESCRIPTION OF EMBODIMENTS OF THE INVENTION

Figure 1:
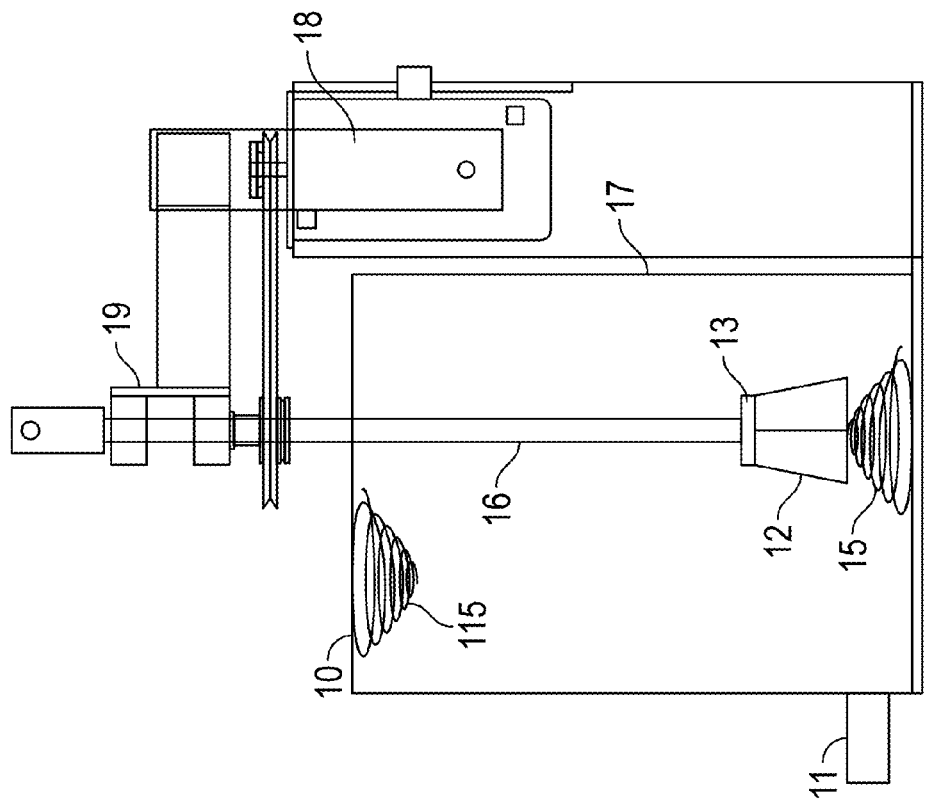
FIG. 1 is a schematic illustration of an improved impeller and gas dispersion device shown in connection with a mixing vessel.

Embodiments of the impeller of the present apparatus and method minimize disruption to impeller discharge flow, and facilitate formation of a controlled low shear vortex at an intake region of the impeller and a corresponding mirrored low shear vortex in the discharge region of the impeller. The formation of these low shear vortices provides a stable fluid circulatory flow in which gas or other flowable materials can be introduced to be entrained and dispersed or dissolved into a liquid mixture. Thus, the present apparatus and method may be used to introduce and entrain gas bubbles into liquid mixtures that require a significant length of time to consume the gas. Embodiments of the present invention entrain gas bubbles via the impeller blades directly into the impeller discharge flow to improve the entrainment and dispersion of the gas into a liquid mixture. The number, size and location of orifices provided in the blades for injecting the gas may be varied to control the flow of gas. In addition, the size of the gas bubbles may be varied by changing rotational speeds of the impeller and gas pressure such that the gas bubbles may either be of a small enough size to be entrained in a circulatory flow, or be allowed to grow into larger gas bubbles and escape the circulatory flow. In other embodiments gas conduits or channels may be built into the blades, or the blades themselves may be made hollow with apertures or orifices to allow the discharge of gas flow directly into the discharge flow created by the impeller. This promotes entrainment of the gas in the circulatory flow while the gas is consumed or absorbed by the liquid mixture. This reduces the need for large, high energy compressors normally used to inject gas into a vessel, and enables the use of smaller compressors.

As an illustrative example, algae have a known consumption rate of $CO_2$, and if the bubbles are uniformly dispersed in a known algae concentration at a rate commensurate with the consumption rate of the algae, the release of escaped $CO_2$ to the surface of the tank can be largely eliminated. In froth flotation, a method of extracting minerals from ore, it is necessary to allow bubble entrainment to have a finite period of time and allow bubbles attached to minerals a chance to surface. The present apparatus and method can control this entrainment time by changing the speed of the impeller, the pressure of the gas, and the number, size and location of the orifices on the blades. Entrainment time is a factor in industrial applications, and although the present disclosure focuses on maintaining entrainment, it should be understood that in cases where entrainment time is required to be limited, the present apparatus and method will accommodate this as well.

More generally, it is a function of the present apparatus and method to disperse and utilize gas in a liquid by creating controlled low shear vortices and entraining the gas in the circulatory liquid flow for a longer period of time. In an embodiment, the apparatus and method may utilize a means for injecting gas directly into the liquid mixture via the impeller blades and upper hub assembly. In another embodiment, gas is injected into the liquid through the shaft. The mixture of small gas bubbles and liquid is treated as a single fluid, rather than a two phase fluid, and a low pressure differential is created as the liquid flow traverses through the low shear vortex, thereby reducing gas expansion.

While the presently disclosed apparatus and method is applicable to a wide range of applications, it is particularly effective for liquid mixtures containing organic materials such as algae, blood plasma, and pharmaceuticals which may require a lower mixing speed in order to preserve and maintain their useful properties. As an illustrative example, in the context of an algae reactor vessel containing a liquid algae mixture, the present apparatus and method may be used to entrain $CO_2$ bubbles directly into low shear vortices and a circulatory flow created by the impeller, and retain the gas bubbles in the algae liquid mixture for a significantly increased amount of time until the $CO_2$ bubbles are consumed by the algae in the reactor vessel. The entrainment of $CO_2$ bubbles in the algae liquid mixture may be controlled by a combination of the mixing speed to create a controlled low shear vortex, and also by controlling the flow of $CO_2$ gas into the liquid flow such that the algae have sufficient capacity to absorb the $CO_2$ gas. The inventor has found through experimentation that the presently disclosed apparatus and method results in a significant increase in $CO_2$ consumption over prior apparatus and methods which allow far more $CO_2$ gas bubbles to rise and escape before they are consumed by algae. In one trial, the inventor observed an increase in $CO_2$ consumption rate of almost five times the consumption rate of prior algae reactor vessels. As a result, this apparatus and method may remove significantly more waste $CO_2$ from the atmosphere in a given period of time, and the algae may be grown and harvested faster to produce bio fuel from the harvested algae.

Thus, the apparatus and method of the present disclosure is suitable for better utilization of the injected gas from an outside source and entraining it for a period of time in a liquid or liquid mixture so as to complete its absorption or consumption. The apparatus and method is particularly useful for broader applications where gas is injected into liquid to create a homogenous mixture, to consume a gas, to transform a liquid, and to reduce or eliminate the occurrence of excessive surface turbulence. Another limitation of current mixing techniques, especially when mixing low-viscosity liquids, is the requirement for the use of baffles in the mixing vessel in order to disrupt the solid-body like rotation that occurs with those techniques. The present improved apparatus does not require baffles, resulting in simpler operation eliminating the need to clean baffles.

Shown in FIG. 1 is a schematic illustration of an embodiment of an impeller and gas dispersion device of the present invention. A mixing vessel 10 is adapted to receive a liquid or liquid mixture. Shown partly contained within mixing vessel 10 is an impeller assembly including an impeller 12, upper hub assembly 13, impeller shaft 16, gear box 18 and drive unit 19. Mixing vessel 10 is not limited to a particular geometry. However, it has been found that because solid-like body rotation of a liquid or liquid mixture may result in a circular vessel, in order to maintain a sufficient circulatory flow of liquid, a non-circular or non-cylindrical mixing vessel may be more suitable. If the mixing vessel 10 is circular, it is preferable that the impeller 12 be situated off center in the mixing vessel 10. This impedes any rotational flows caused by the circular geometry of a vessel, thus utilizing mixed radial and axial flows to impede the formation of a uniform body rotation within the mixing vessel, and thereby eliminating the need for baffles.

Figure 2:
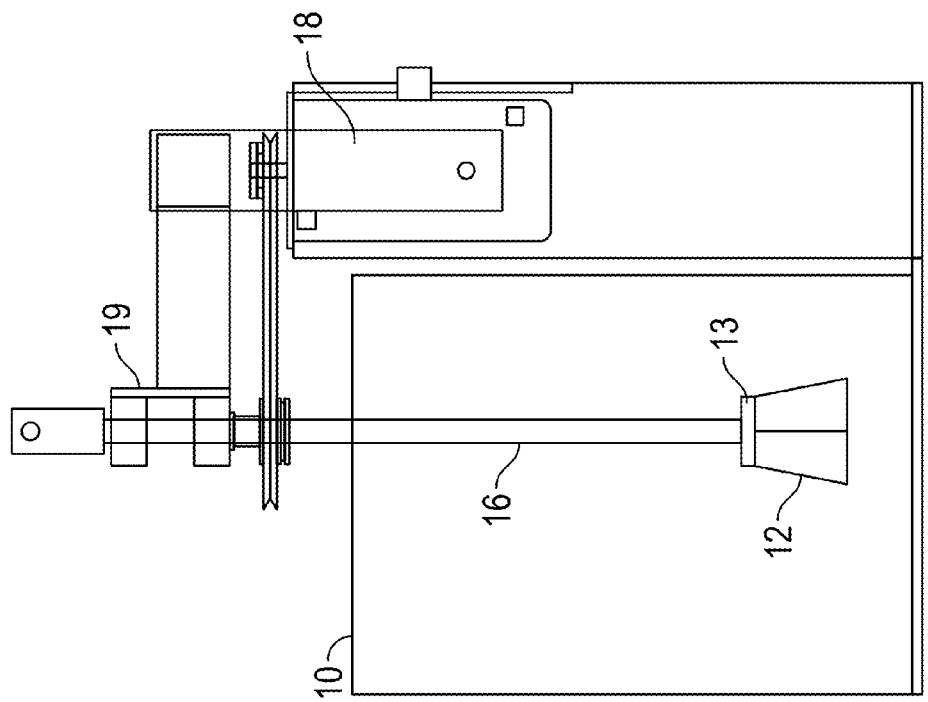
FIGS. 2 and 3 are detailed schematic illustrations of an improved impeller and gas dispersion device in operation.
Figure 3:
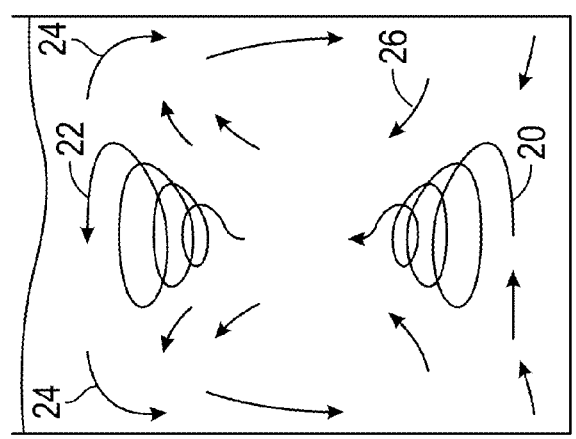

FIGS. 2 and 3 are detailed schematic illustrations of an impeller and gas dispersion apparatus 17 in operation. In addition to the parts already described above, FIG. 2 shows a controlled low shear vortex 15 preferably formed near the intake region of impeller 12. A corresponding mirrored vortex 115 is preferably formed near the surface of the liquid or liquid mixture, as the impeller drives the liquid or liquid mixture in a circulatory path within mixing vessel 10. As shown in FIG. 3, apparatus 17 preferably produces a low shear vortex 20 with both a radial and axial flow, and a helical conical configuration of the low shear vortex that provides suction and draws liquid and particles in the intake zone 26 inwardly toward the eye of impeller 12 (FIG. 2). Impeller 12 preferably comprises upper hub assembly 13 that provides a flow through discharge slot design that only minimally disrupts the exit flow 22. As shown, exit flow 22 also has a helical shape and both a radial and axial component. Apparatus 17 preferably produces an impeller discharge flow 24 up and away from the central axis of rotation, thus allowing the discharge flow 24 to break away from the impeller 12 and be drawn down again into the intake zone 26 of impeller 12. The flow is preferably further guided by discharge flows pushing away the upper flow and maintaining its path along and spirally around the vessel.

The creation of a controlled low shear vortex 20 forms a region of low pressure differential between the interior and exterior aspects of the impeller assembly, thereby proving a sufficiently stable zone of transition between the impeller intake region and the impeller discharge region for gas bubbles to reside and be further pumped without stalling or flooding the impeller. Because of the low pressure differential between the intake and discharge side of the impeller, the two phase (gas and liquid) mixture can be effectively treated as If it were a single phase fluid (liquid), and therefore the gas bubble particles are treated as liquid particles, thereby being able to mix them and entrain them. This characteristic of the presently disclosed apparatus and method doesn't work in conventional propellers or turbines, especially in shear sensitive materials. The impeller discharge flow preferably produces low turbulence surface action and sufficient mixing between the axis of rotation and the impeller discharge zone so as reduce any circulatory dead zones in the vessel. Thus, the low pressure differential and stable zone of transition provide a low shear method of mixing that prevents foaming or shear damage to biological materials, pharmaceuticals, or other shear sensitive liquids or liquid materials.

Figure 11:
FIG. 11 is a photograph of an impeller of the present invention showing fluid flow patterns.

A photograph showing the fluid flow of an impeller of the present is shown in FIG. 11. As the impeller rotates, a prewhirl condition with both a radial and axial component is formed, similar to an inverted tornado. This prewhirl condition rotates the fluid into a helical spiral flow and pulls material from the bottom of the tank into the impeller, where it is discharged outwardly through the openings between the blades. As can be seen in FIG. 11, colored fluid enters the impeller from below and when it reaches a certain height is discharged approximately horizontally to the exterior of the impeller.

Figure 4:
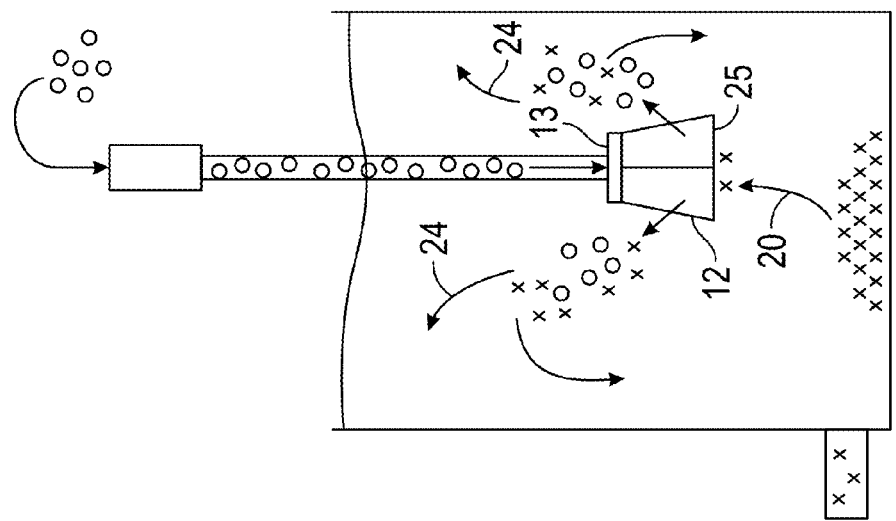
FIG. 4 is a schematic representation of the flow of gas mixing with fluid by operation of the improved impeller and gas dispersion device in a chamber.

FIG. 4 is a schematic representation of the flow of gas mixing with fluid by operation of an embodiment of the improved impeller and gas dispersion device of the present invention in a chamber. Particles are preferably transported to mixing vessel 10 through input conduit 11. Low shear vortex 15 (as shown in FIG. 2) created by the rotation of impeller 12 pulls settled particles (shown as x's in FIG. 4) from the vessel bottom, suspends them and introduces them to a stream of gas bubbles to attach to and absorb. The stream of gas bubbles can be introduced into the discharge flow stream by any suitable means, including by injection from a source adjacent the discharge flow stream, or by structural adaptation of the impeller blades to inject gas bubbles into the liquid discharge zone of the impeller, as detailed below.

A significant difference between the present apparatus and method and the prior art is that the impeller design of the present apparatus creates a forced vortex unrelated to swirling created in circular tanks. Prior art devices that produce swirling and rotational vortexes generally do so by utilizing the circular geometry of the vessel, and rotating the impeller in the centre of the circular tank. Rotating fluid preferably has a highly concentrated radial component to the flow, and particles suspended therein have a relatively low mixing advantage due to the fact that the particles tend to rotate at the same speed as the vortex, resulting in a low mixing effect due to the fact that everything is moving together. Such solid-body like rotation is typically circumvented with the use of baffles in the tank. In contrast, using the present apparatus and method, more efficient mixing is provided by inducing a differential between moving liquid and particles and non-moving liquid and particles, and producing a mixed flow with both axial and radial components that does not rely on vessel geometry. Thus, the present apparatus and method does not rely on the geometry or shape of the vessel in which it operates and can operate without the use of baffles, and are thus very scalable.

Still referring to FIG. 4, the intake flow entering the larger diameter of the impeller 12 has both a radial and axial component and can be described as an inverted vortex 20, best seen in the flow diagram in FIG. 3. The upward intake flow is preferably conical and helical. Fluid and particles entrained in the fluid move along a helical path that reduces in diameter to approximately that of the diameter of the intake orifice 25 of the impeller. The intake vortex preferably has a continually widening bottom diameter dependent on the distance of impeller bottom from the tank bottom. Fluid enters the impeller 12 in a swirling fashion and preferably completes its helical path along the interior sides of the generally conically arranged blades of the impeller 12, while continually being ejected to the outside of the blades of the impeller 12. Flow is ejected on an angular path generally opposite to the angle of the conical impeller, and continues as an expanding, helical flow 22 that breaks away from the axis rotation toward the vessel side wall where it then continues down the vessel wall to be reintroduced into the intake. Upper hub assembly 13 of impeller 12 is designed to reduce collisions of the intake flow with upper hub assembly 13 which may produce an undesirable backflow which will disrupt the low shear vortex. Upper hub assembly 13 provides attachment of circumferentially attached blades 14, while reducing surface area exposed to upward axial flows. As described in more detail below, the design of upper hub assembly 13 preferably allows a stable transition from the intake helical flow to the discharge helical flow and reduces entrained particles from collision with each other and the mechanical structure of the device. The configuration of upper hub assembly 13 and the blade assembly preferably permits a smooth flow transition between the intake flow to the impeller blades and the impeller discharge flow.

Figure 5B:
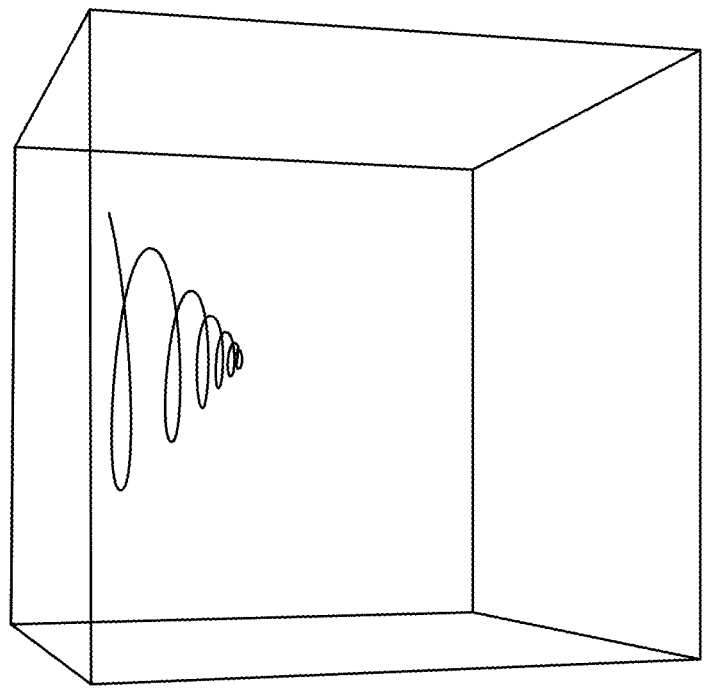
FIGS. 5A and 5B are schematic illustrations of a conical helix of the low shear vortices formed in the impeller intake region and in the impeller discharge region, respectively.
Figure 5A:
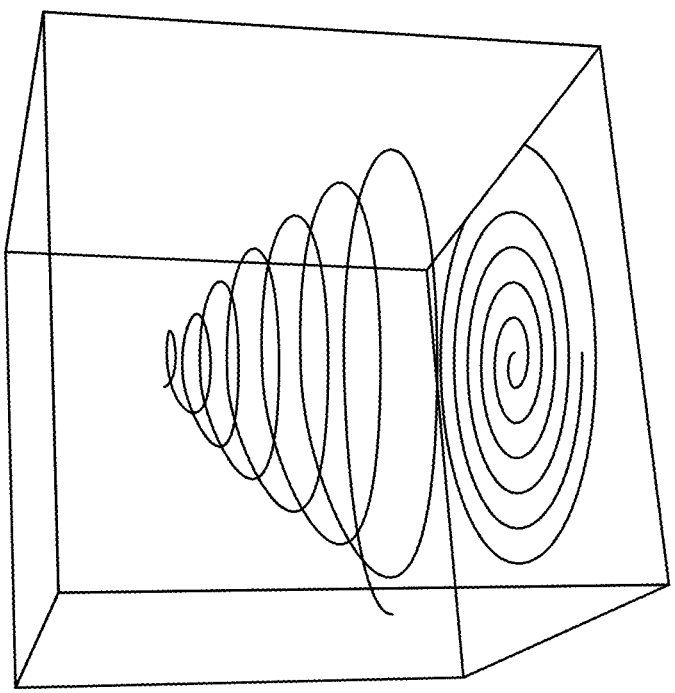

FIGS. 5A and 5B are schematic illustrations of a conical helix of the low shear vortices formed in the impeller intake region and in the impeller discharge region respectively. In FIG. 5A, the conical helix of the low shear vortex formed near the impeller can be described by the equation:

$$\begin{bmatrix} x \\ y \\ z \end{bmatrix} = \begin{bmatrix} t\cos(6t) \\ t\sin(6t) \\ t \end{bmatrix}, t = 2 \ldots 45$$

Discharge flow 22 is an expanding, inverse of this intake flow, with both a helical and conical shape, which gradually falls away as fluid momentum is lost and resistance is met with the fluid immediately present in the path of the discharge flow. The upper hub assembly 13 preferably enables a free flowing transition of intake flow to discharge flow and, in a suitably sized vessel, creates a highly organized circulatory flow pattern to be developed after a number of minutes. The upper hub assembly 13 preferably enables a free release of a conical helix flow, and provides minimal obstruction to particles and fluid flow discharge. The present apparatus and method initiates and maintains this conical helix flow, and the upper hub assembly 13 and attached blades allow a matched discharge flow without causing a transitional disruption, which is key to a low shear mixing device suitable for organic suspension mixing and pumping. FIG. 5B shows the corresponding mirrored conical helix formed in the impeller discharge region. As the discharge flow 22 pushes up and into the zone of fluid above the upper assembly plate, it breaks away from the axis of rotation toward the vessel sides, and is diverted back down from the discharge side plane, and in a circular and helical fashion continues back down the vessel wall toward the intake zone of the impeller to be reintroduced with increased whirl and momentum, thereby reducing the energy required.

Figure 7:
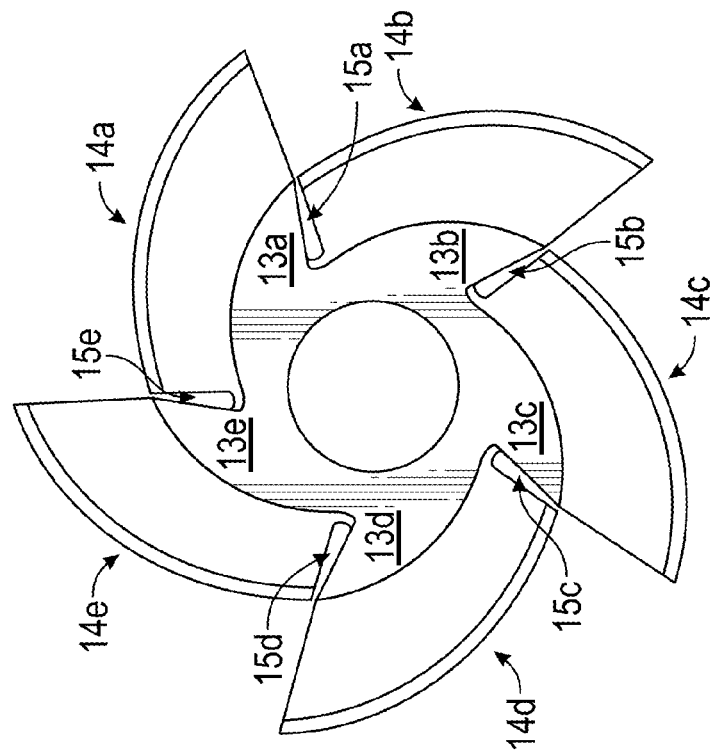
FIGS. 6, 7 and 8, are top, bottom, and perspective views respectively of an impeller of the present invention.
Figure 6:
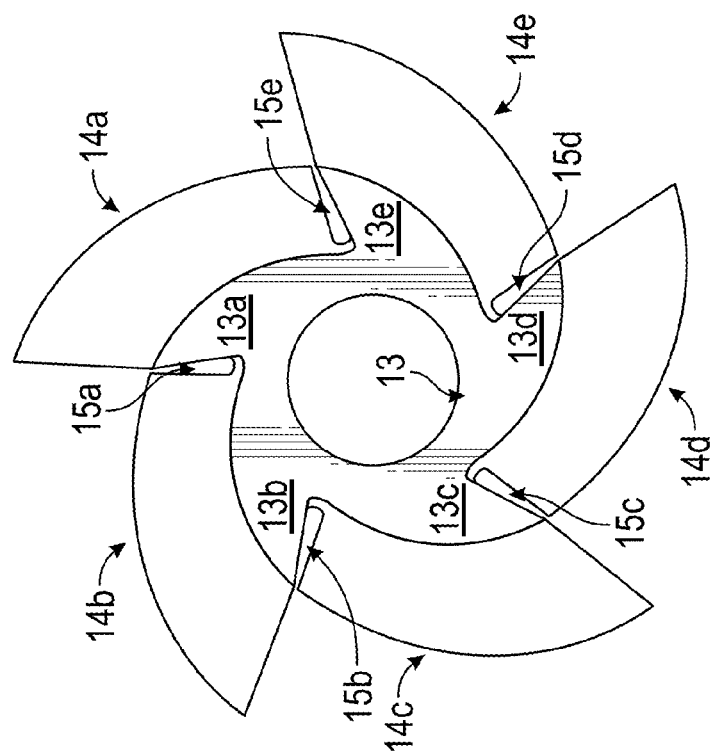
Figure 8:
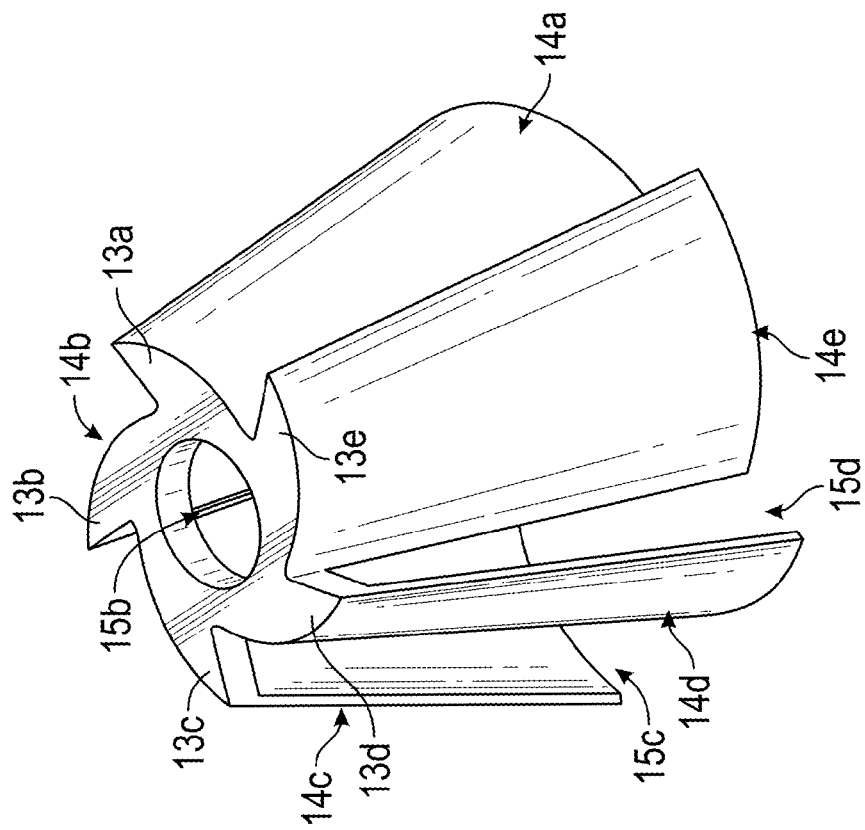

Now referring to FIGS. 6, 7 and 8, shown are illustrative drawings of the impeller 12 of the present apparatus according to a number of different views. More particularly, FIG. 6 shows a plan view of an upper hub assembly 13 in accordance with an embodiment of the present apparatus. The design of impeller 12 of the present apparatus is in some ways similar to the impellers described in U.S. Pat. No. 5,314,310 (Bachellier '310) and U.S. Pat. No. 5,938,332 (Bachellier '332), previously granted to the present inventor and incorporated herein by reference. Used as mixing devices, the impellers in Bachellier '310 and '332 are similar to the impeller 12 of the present apparatus in that they also contain a plurality of blades similarly circumferentially attached around a central axis. However, the impeller 12 of the present disclosure is different from the impellers in Bachellier '310 and '332 in that the upper hub 13 is designed such that the upper hub 13 only minimally disrupts the liquid flow between a low shear vortex formed at the intake to the impeller 12 and a corresponding mirrored vortex formed by the impeller discharge flow. More particularly, as shown in FIG. 6, the upper hub assembly 13 forms a shape comprising a plurality of arms or fins 13a, 13b, 13c, 13d and 13e that are preferably evenly spaced apart. The shape of the fins 13a-13e generally follows the curved profile of the blades 14a, 14b, 14c, 14d and 14e, where the blades 14a-14e attach circumferentially to the upper hub assembly 13 along the outside curved edge of each arm or fin. This design maintains the integrity of the forced vortex and reduces particle damage and shear at impeller intake and discharge. Upper hub assembly attaches the blades 14a-14e at angles such that radially extending discharge slots 15a, 15b, 15c, 15d and 15e are formed between the blades 14a-14e to allow liquid to flow past the impeller 12 into the impeller discharge region. The result is that the blades 14a-14e attached to the upper hub assembly 13 form a generally conical shape, as shown in FIG. 8, which closely profiles the intake vortex and provides a beveled or cambered edge to relieve transitional flow stresses at point of contact. The impeller preferably provides a smooth liquid flow through the impeller and out the discharge slots 15a-15d. Thus the upper hub assembly 13 not only acts as a point of attachment for the blades 14a-14e in a desired configuration, but also provides a minimally disruptive liquid flow transition between the impeller intake region and the impeller discharge region. Without this modified design, increased interference may result in disrupting the low shear vortex and creating an undesirable pulsing effect instead due to the increased pressure differential.

In a given application, the discharge velocity of the liquid flow created by the impeller 12 may preferably be some multiple of the speed of intake flow across the impeller blade surfaces. In order to achieve a desired discharge velocity while maintaining a controlled low shear vortex, the size of the impeller 12, and the speed of rotation of the impeller 12 may be selected and controlled. For example, for an impeller 12 with a 4-inch diameter, a minimum rotation speed of approximately 230 RPM may be required to create the desired low shear vortex. Additionally, the size and shape of the mixing vessel 10 may be taken into account to determine the size of the impeller 12 and the rotational speed necessary. In larger mixing vessels 10, multiple impellers 12 may be required in order to achieve a sufficient circulation of liquid flow without dead zones.

Figure 9:
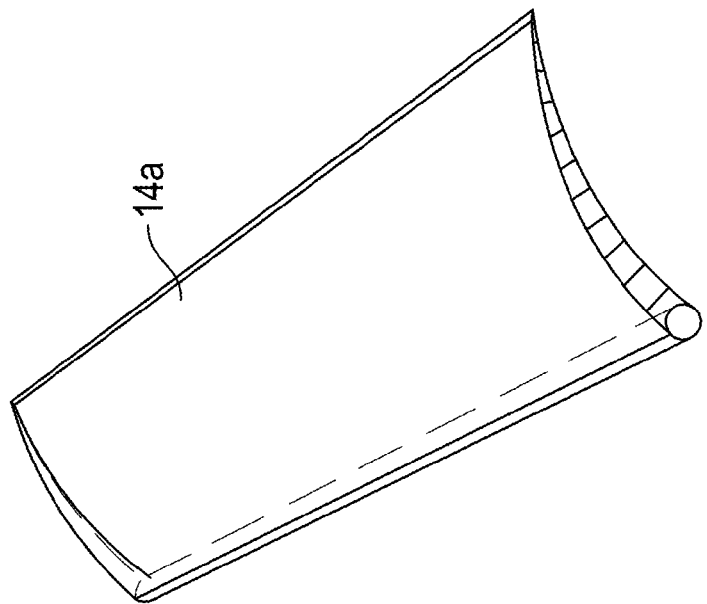
FIG. 9 shows an illustrative embodiment of a hollowed blade.
Figure 10:
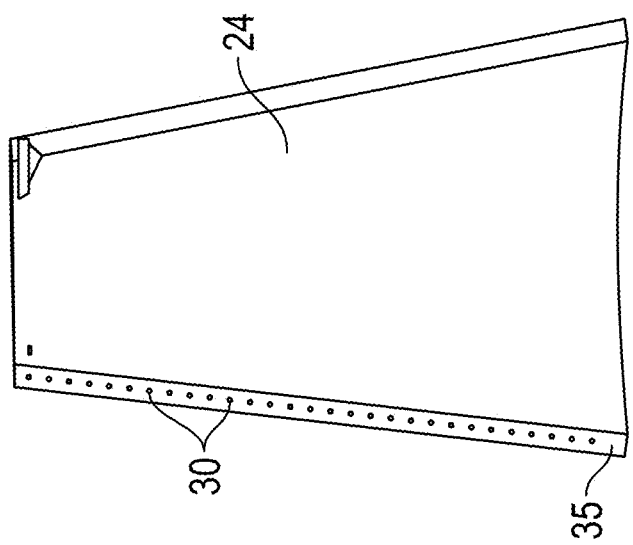
FIG. 10 is a schematic of a blade of the present invention showing orifices along the blade edge for discharging gas.

FIG. 9 is an illustrative embodiment of a hollowed blade, which may be used to introduce gas directly into the liquid flow passing through the impeller. In this case, the upper hub assembly 13 may receive air from impeller shaft 16, as shown in FIG. 4, and may be adapted to act as a gas manifold to direct gas into one or more of the blades 14a-14e. In this manner, gas may be introduced at a desired entry point and the power otherwise required for a compressor to introduce gas in larger volumes using a sparger may be significantly reduced or eliminated. FIG. 10 shows another view of a blade 24 comprising one or more orifices 30 disposed along discharge edge 35. Orifices 30 can be used to inject gas into the region surrounding the impeller and/or directly into the flow of fluid entering into the impeller, thereby enhancing dispersion efficiency of the gas in the fluid. The diameter, position and number of orifices provided in the blades 24 for discharging gas may be determined according to the requirements for a particular application. Positioning the orifices on the fluid discharge side of the impeller 12 preferably provides an effective way to disperse gas directly into the impeller discharge flow.

This solution avoids limitations of some existing designs such as the Rushton Turbine, which creates very low pressure zones in blade cavities rotating at high speed. In a Rushton Turbine, gas traverses into a low pressure zone of the blades, and as the gas expands it is then introduced into the liquid. But the Rushton Turbine uses a high speed, high shear method which may destroy the useful properties of organic materials or pharmaceuticals. Thus, the Rushton Turbine is not suitable to use with an algae reactor containing a liquid algae mixture, for example.

An illustrative example of an application in which the disclosed apparatus and method may be used relates to the capture of waste $CO_2$ from smokestack emissions into a tank of algae slurry, providing the algae with $CO_2$ and nitrates for their growth process. Successful growth of algae in tanks have been limited using prior art devices because as the tank size increases, so does the size of propeller required to maintain an equal distribution of gas and nutrients. The present apparatus and method provides significant scalability and an economical solution for maintaining algae suspension and $CO_2$ distribution. Also, the present apparatus and method facilitates a way to provide an optimum rate of flow of $CO_2$, which would match the rate of consumption of $CO_2$ by the algae, taking into account the characteristic rapid growth rate of algae, which can double its mass every 12 hours or so. Algae has a particularly unique property, in that when an algae strand dies from damage or lack of nutrients, its neighbor dies, producing a cascade effect that will kill an entire bioreactor very quickly. Prior art devices do not have impellers suitable for use on a large scale to prevent algae damage. Prior art devices also exhibit a significant pressure differential between the intake and discharge zones, which may cause stalling and flooding, and lower the efficiency of the mixing device. The impeller of the presently disclosed apparatus and method has a lower pressure differential within the impeller and outside the impeller, and therefore allows the stable movement of gas entrained liquid. Further, the present disclosure provides an upper hub assembly on the impeller that does not significantly disrupt the transition zone between intake and discharge regions of the impeller, and thus allows for a steady state discharge flow with low shear characteristics.

Another application of the invention is for use in flotation cells. As the gas and particles are ejected from the discharge side of the impeller of the present apparatus and method, particles can be attached directly to gas bubbles and the size and speed of the bubble attaching to the particle can be controlled as a function of rotational speed and gas pressure. As the rotational speed of the impeller drops, the strength of the circulatory flow decreases and allows the bubbles to escape the flow pattern. By introducing the gas through the discharge side of the impeller blades into the flow, energy efficiencies can be obtained. Further, at appropriate speeds, embodiments of the present impeller can create a low shear vortex approximately 30 times its diameter, and pull settled particles up from a tank bottom and discharge them away from the impeller into the gas stream.

In another embodiment, the present apparatus and method may be used in Advanced Oxidation Processes (AOP). AOP is a chemical treatment method for water designed to remove organic and inorganic materials from water though an oxidation process, and utilizes ozone, oxygen and peroxide with a goal to reduce chemical toxins in water to a lower level and allow it to be released back into the ecosystem. The present apparatus and method can be used to inject and entrain the gases into the water and oxidize it, and would also reduce the possibility of off gassing.

Embodiments of the present apparatus and method can be applied in fermentation tanks used in pharmaceutical and chemical manufacture, where thorough mixing and gas bubble distribution are important in large tanks. The presently disclosed apparatus and method requires approximately half the power of prior art propeller or turbine systems, and cuts blend times in low viscosity, water-like materials by up to a factor of five.

Embodiments of the present invention produce extremely low thermal transfer to the liquid during mixing. Temperature increases of the liquid due to mixing can otherwise adversely affect biological materials and pharmaceuticals during processing.

The apparatus and method of the present invention may also be utilized to disperse flowable nanoparticles into a medium. In this case, it will be appreciated that it is important to prevent agglomeration. Agglomeration or clumping of nanoparticles negatively affects the properties of a mixed composite material. Similarly, smaller gas bubbles can agglomerate to become larger bubbles, which may more easily overcome entrainment and escape from a mixer. This results in waste of the gas, and for certain important methods involving mixing of gas in a medium, there can be a bigger problem if gas is poisonous. This is a significant reason why an otherwise effective water treatment method, namely ozonation, is not used more broadly, or if it is used then reliable fume hoods or other containment methods are required. The present apparatus and method may thus also be utilized for ozonation because of the effective entrainment of gases in the mixing vessel.

Due to the scalability of the presently disclosed apparatus and method, larger systems may be built to match high output of $CO_2$ produced by industrial plants such as coal fired electric plants, cement plants, and steel manufacturing plants. Efficient gas dispersion in liquid also enables alternative transport methods of captured $CO_2$ in water or ammonia for transport using tanker trucks or underground pipes.

Thus, in an aspect, there is provided a method and apparatus for dispersing and entraining gas particles, controlling the residence time, absorption and release of dispersed and entrained gas particles without losing gas utilization efficiency from escaping surface gas events. A mechanical, rotating plurality of hollowed blades that induce both an axial and radial controlled circulatory flow and provide a means of gas introduction into the discharge flow that has a helical, axial and radial outward flow from the axis of rotation and allows entrained gas bubbles to be trapped as particles and recirculated by means of a circulatory flow back into the intake vortex of said mechanical, rotating plurality of blades. The flow is characterized by a forced intake vortex caused by a low pressure zone with a radial component, and subsequent axial component drawing fluid in a circular fashion toward the eye of the rotating device and impelling fluid. The gas entrained flow, while passing through the discharge outlet regards the flow as a single phase fluid due to a low pressure differential between the intake side of the rotating blade and the external side of the rotating blade, preventing gas particles from expansion and or compression resulting in a stalled or flooded condition. The flow is further characterized as leaving the rotating body at an angle falling between perpendicular to the axis of rotation and the vessel wall, resulting in low surface turbulence and the formation of a circulatory flow that allows the fluid to move down the vessel wall to be pulled in again by the intake vortex. The gas introduction providing sufficiently small enough bubbles to be entrained by a strong circulatory flow, that strength determined by rotational speed and blade angle allowing the entrainment or controlled release of gas bubbles from the liquid in the vessel.

In an embodiment of the present invention, the mechanical impeller causes a rotational flow that has both an axial and radial component in the form of a conical helix, with the large diameter of the conical helix being the furthest away from the impeller.

In another embodiment, the mechanical impeller blades are attached circumferentially using a plate that minimizes disruption to the conical helix flow upon discharge.

In another embodiment, in use the mechanical impeller causes a mirror vortex.

In another embodiment, the mechanical impeller is comprised of hollowed blades with openings along the discharge length.

In another embodiment, the mechanical impeller is a conical, squirrel cage type impeller with hollowed blades.

In another embodiment, the mechanical impeller is positioned off centre of the vessel.

In another embodiment, the vessel includes a device for providing gas to be introduced into the liquid.

In another embodiment, the device increases entrainment of gas bubbles increasing gas utilization and absorption.

In another embodiment, the apparatus comprises hollowed blades providing a method of introducing gas into the discharge side of said blades.

In another embodiment, the apparatus comprises a hollowed drive shaft adapted to provide gas to an impeller with circumferentially attached blades to a generally conical impeller.

In another embodiment, the apparatus comprises an upper assembly plate and point of blade attachment that when rotated produces a similar flow pattern to the rotating impeller and does not break the steady flow state of the fluid from intake to discharge and maintains entrained gas bubbles in the circulatory flow.

In another embodiment, the apparatus comprises hollowed blades that have a shape consistent with the sections of a frustum of a cone, each blade having a profile equal to a division of said frustum and that division being the number of blades.

In another embodiment, the apparatus is utilized in a vessel containing shear sensitive, organic based material.

In another embodiment, the apparatus is part of a system to mix CO2 gas into algae to promote algae growth.

In another embodiment, the apparatus is part of a system to inject waste smokestack CO2 and nitrates from industry into algae ponds to reduce CO2 emissions and produce bio fuel.

In another embodiment, the apparatus is part of a system to inject gas into shear sensitive *E-coli* fermentation tanks for production of vaccines.

In another embodiment, the apparatus is a part of a system to inject gas into chemical liquids.

In another embodiment, the apparatus is part of a system to inject gas into fermentation tanks.

In another embodiment, the apparatus is part of a system to inject waste smokestack gas into lime slurry to reduce flu gas emissions.

In another embodiment, the apparatus is part of a system to inject gas into flotation tanks to attach said gas bubbles to precious metal particles for precious metal recovery operations in froth flotation tanks.

In another embodiment, the apparatus is part of a system to inject a gas into water to treat wastewater and potable water sources.

In another aspect, there is provided a method of mixing a two phase liquid as a single phase by having a very low pressure differential between the back and face of said mechanical impeller.

In another aspect, there is provided a method of mixing liquid with gas through entrainment in a conical helical circulatory flow, said method including the steps of placing the liquid(s) in the vessel having both an upper and lower region and inducing an expanding, conical and helical flow pattern, inducing a highly controlled circulatory flow in the liquid with a mechanical impeller rotating in a vertical axis submerged in said liquid with gas being introduced through the rotating shaft into the upper interior opening of the impeller where the hollow drive shaft may continue through the upper plate assembly, bypassing the manifold and allow the injection of gas into the impeller region by utilizing the negative pressure created by the rotating device to pull gas down the drive shaft and dispersing gas into circumferentially attached blades of a generally conical configuration, said manifold and upper point of blade attachment providing a smooth transition between intake conical helical flow and discharged conical helical flow so as not to disrupt said circulatory flow and maintain entrainment of gas bubbles long enough for absorption or consumption to take place in said liquid. The circulatory flow has both a radial and axial component and a larger diameter furthest away from intake side of rotating impeller, and gradually reducing to the same diameter of the intake of rotating impeller, passing through circumferentially attached blades that release gas bubbles into discharge stream and pass through an upper assembly plate for attachment of said blades and providing a non-interfering pathway for a steady state discharge flow of entrained gas bubbles in a liquid. The discharge flow breaks away from the upper assembly plate toward vessel walls and recirculates along vessel side walls back into intake side of said rotating impeller when bubbles of gas are small enough to be entrained, or allows the bubbles or discharge flow to reach the surface in applications that require gas or liquid or a combination of gas and liquid to be transferred to the surface, with control of this bubble size and level of entrainment affected by gas pressure, rotational speed and orifice diameter.

In another aspect, there is provided a method mixing liquid and particles through a conical helical circulatory flow, said method including the steps of placing the liquid and particles in the vessel having both an upper and lower region and inducing an expanding, conical and helical flow pattern, inducing a highly controlled circulatory flow in the liquid with a mechanical impeller rotating in a vertical axis submerged in said circumferentially attached blades of a generally conical configuration, said manifold and upper point of blade attachment providing a smooth transition between intake conical helical flow and discharged conical helical flow so as not to disrupt said circulatory flow and maintain particle mixing and suspension.

In another embodiment, the present apparatus and method may be used in an inline Advanced Oxidation Processes (AOP) whereby multiple impellers are used inline in a pipe and the discharge flow from the first impeller supplies the intake flow of the second impeller and the flow transition and subsequent turbulent zones between multiple impellers creates mixing to introduce advanced oxidation process gas and chemicals such as ozone and hydrogen peroxide either externally through the outside of the pipe using an injection port or internally through a hollow drive shaft. The present apparatus and method can be used to inject and entrain the gases into the water and oxidize it.

In another embodiment, the apparatus is part of a system to mix stagnant water in lakefront beach areas to improve overall water quality and disperse stagnant shoreline water that contributes to bacteria growth and beach closure.

In another embodiment, the apparatus is part of a system to mix stagnant water in lakes suffering from lake anoxia to improve overall oxygen content.

In another embodiment, the apparatus is part of a system to suspend and recirculate silt built up at the mouths of rivers that prevents outflow disruptions from rivers and streams as they enter larger bodies of water.

In another embodiment, the apparatus is part of a system to inject a gas into oil industry wastewater or produced water to recover hydrocarbons.

It will be obvious to those skilled in the art that modifications of the improved impeller and gas dispersion device of the present disclosure may be adopted without departing from the spirit of the present disclosure. Changes may be made in the combination and arrangement of the various parts and elements, described herein without departing from the spirit and scope of this invention. It will be apparent that the scope of the present disclosure is limited only by the claims set out herein below. Although the invention has been described in detail with particular reference to the disclosed embodiments, other embodiments can achieve the same results. Variations and modifications of the present invention will be obvious to those skilled in the art and it is intended to cover all such modifications and equivalents. The entire disclosures of all patents and publications cited above are hereby incorporated by reference.

What is claimed is:

1. An impeller apparatus comprising:
   a plurality of blades circumferentially mounted in a conical fashion at their proximal ends to arms of a separate upper hub assembly connected to a drive unit, the blades' distal ends being flared out to circumscribe a diameter larger than the upper hub assembly, the blades having a forward intake end directed to the centre of the apparatus and a rearward discharge end and being tapered such that the forward intake end is enlarged relative to the rearward discharge end,
   whereby in use the impeller forms in the liquid mixture a low shear intake vortex at the centre of the impeller, and a mirrored low shear vortex at a discharge region of the impeller, thereby to form a circulatory flow of the liquid mixture in the vessel;
   wherein intersections of adjacent said arms each form an acute angle.

2. The apparatus of claim 1 wherein the drive unit comprises a motor and is connected to the impeller via a shaft.

3. The apparatus of claim 1 wherein the shaft is hollow with outlets placed at the shaft's connection with the impeller to allow the introduction of gas.

4. The apparatus of claim 1 wherein the blades are hollow with outlets placed along the edges of the blades to allow the introduction of gas.

5. The apparatus of claim 4 wherein the outlets are placed along the forward edges of the blades.

6. The apparatus of claim 4 wherein the outlets are placed along the rearward edges of the blades.

* * * * *